(12) United States Patent
Li et al.

(10) Patent No.: US 12,337,192 B2
(45) Date of Patent: Jun. 24, 2025

(54) METHOD AND DEVICE FOR DETERMINING ROTATION SPEED OF GANTRY, AND MEDICAL EQUIPMENT

(71) Applicant: OUR UNITED CORPORATION, Xi'an (CN)

(72) Inventors: Jinsheng Li, Xi'an (CN); Qinglong Zhang, Xi'an (CN); Long Chen, Xi'an (CN); Hong Cheng, Xi'an (CN); Hongbin Zhao, Xi'an (CN); Shifeng Fan, Xi'an (CN)

(73) Assignee: OUR UNITED CORPORATION, Xi'an (CN)

( * ) Notice: Subject to any disclaimer, the term of this patent is extended or adjusted under 35 U.S.C. 154(b) by 330 days.

(21) Appl. No.: 17/822,238

(22) Filed: Aug. 25, 2022

(65) Prior Publication Data

US 2023/0068470 A1    Mar. 2, 2023

(30) Foreign Application Priority Data

Aug. 25, 2021   (CN) .......................... 202110983426.3

(51) Int. Cl.
*A61N 5/10*   (2006.01)

(52) U.S. Cl.
CPC ............. *A61N 5/10* (2013.01); *A61N 5/1048* (2013.01); *A61N 5/1047* (2013.01)

(58) Field of Classification Search
CPC ...... A61N 5/1048; A61N 5/10; A61N 5/1047; A61N 5/103; A61N 5/1071; A61N 5/1067; A61N 5/1049; A61N 5/1031; A61N 5/1042; A61N 5/1043; A61N 5/1077; A61N 2005/1087; A61N 5/1036; G06T 7/11; G06T 2207/30164; B23K 26/38; B23K 26/02; B23K 2101/06; G01R 35/005; G06F 3/03543; G06F 3/0383; A61B 6/032; A61B 6/44; A61B 6/54; A61B 6/4071; G16H 20/40; H05G 1/44
USPC .......................................................... 378/65
See application file for complete search history.

(56) References Cited

U.S. PATENT DOCUMENTS

| | | | |
|---|---|---|---|
| 2016/0299088 A1* | 10/2016 | Zoboyan | A61B 6/54 |
| 2017/0291043 A1* | 10/2017 | Ju | A61N 5/1048 |
| 2018/0014808 A1* | 1/2018 | Masuda | A61B 6/032 |
| 2019/0150878 A1* | 5/2019 | Smith | A61B 6/5205 |
| 2019/0255362 A1* | 8/2019 | Voronenko | A61N 5/1071 |
| 2019/0329073 A1* | 10/2019 | Meltsner | A61N 5/1077 |
| 2020/0054895 A1* | 2/2020 | Ranganathan | G16H 20/40 |
| 2021/0252307 A1* | 8/2021 | Kontaxis | A61N 5/1047 |

* cited by examiner

Primary Examiner — Irakli Kiknadze
(74) Attorney, Agent, or Firm — Kolitch Romano Dascenzo Gates LLC

(57) ABSTRACT

Provided is a method for determining a rotation speed of a gantry. The method includes: acquiring control information of the gantry, wherein the control information of the gantry includes: leaf information and dose information of control points; determining the rotation speed of the gantry and dose rates at the control points based on the leaf information and the dose information of the control points; and adjusting the rotation speed of the gantry based on the dose rates at the control points and a maximum equipment dose rate.

20 Claims, 3 Drawing Sheets

METHOD AND DEVICE FOR DETERMINING ROTATION SPEED OF GANTRY, AND MEDICAL EQUIPMENT

CROSS-REFERENCE TO RELATED APPLICATION

This application is based on and claims priority to Chinese Patent Application No. 202110983426.3 filed on Aug. 25, 2021 and entitled "METHOD AND DEVICE FOR DETERMINING ROTATION SPEED OF GANTRY, AND MEDICAL EQUIPMENT," and the disclosure of which is herein incorporated by reference in its entirety.

TECHNICAL FIELD

The present disclosure relates to the field of radiation therapy, and in particular, relates to a method and device for determining a rotation speed of a gantry, and medical equipment.

BACKGROUND

Generally, in radiation therapy, medical equipment employs a dynamic therapy plan, which ensures an efficient therapy of a case by cooperation operation of a gantry, a dosing system, and a multi-leaf grating. Specifically, the dynamic therapy plan is based on a principle of an arc therapy. In the rotation of the gantry, the dosing system uniformly delivers a dose to a tumor target region, and the multi-leaf grating keeps moving to adjust a portal shape of rays.

SUMMARY

Embodiments of the present disclosure provide a method and device for determining a rotation speed of a gantry, and medical equipment. The present disclosure is implemented as follows.

According to some embodiments of the present disclosure, a method for determining a rotation speed of a gantry is provided in the embodiments of the present disclosure. The method includes: acquiring control information of the gantry, wherein the control information of the gantry includes: leaf information and dose information of control points; determining the rotation speed of the gantry and dose rates at the control points based on the leaf information and the dose information of the control points; and adjusting the rotation speed of the gantry based on the dose rates at the control points and a maximum equipment dose rate.

According to some embodiments of the present disclosure, a device for determining a rotation speed of a gantry is provided in the embodiments of the present disclosure. The device includes: a processor, a memory, and one or more programs or instructions stored on the memory and executable on the processor, wherein the processor, when loading and executing the one or more programs or instructions, is caused to perform the method according to above embodiments.

According to some embodiments of the present disclosure, an apparatus for determining a rotation speed of a gantry is provided in the embodiments of the present disclosure. The apparatus includes: an acquiring module, a determining module, and an adjusting module, wherein the adjusting module is configured to acquire control information of the gantry, wherein the control information of the gantry includes: leaf information and dose information of control points; the determining module is configured to determine the rotation speed of the gantry and dose rates at the control points based on the leaf information and the dose information of the control points; and the adjusting module is configured to adjust the rotation speed of the gantry based on the dose rates at the control points and a maximum equipment dose rate.

According to some embodiments of the present disclosure, medical equipment is provided in the embodiments of the present disclosure. The medical equipment includes a processor and a memory configured to store one or more programs or instructions executable on the processor, wherein the processor, when loading and executing the one or more programs or instructions, is caused to perform the method according to above embodiments.

According to some embodiments of the present disclosure, a readable storage medium is provided in the embodiments of the present disclosure. The readable storage medium stores one or more programs or instructions, wherein the one or more programs or instructions, when loaded and executed by a processor, cause the processor to perform the method according to above embodiments.

According to some embodiments of the present disclosure, a chip is provided in the embodiments of the present disclosure. The chip includes a processor and a communication interface, wherein the communication interface is coupled to the processor, and the processor, when loading and executing one or more programs or instructions, is caused to perform the method according to above embodiments.

According to some embodiments of the present disclosure, a computer program product is provided in the embodiments of the present disclosure. The computer program product includes one or more instructions, wherein a processor, when loading and executing the one or more instructions, is caused to perform the method according to above embodiments.

DETAILED DESCRIPTION

Figure 1:
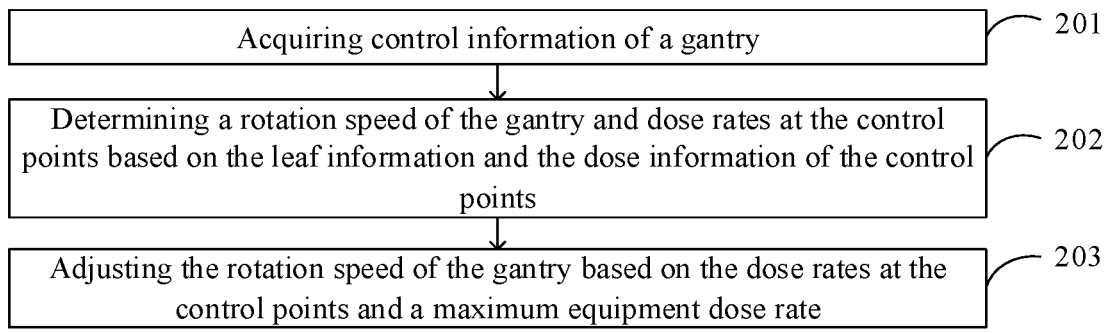
FIG. 1 is a flowchart of a method for determining a rotation speed of a gantry according to some embodiments of the present disclosure.

The technical solutions of the embodiments of the present disclosure are clearly described hereinafter in combination with the accompanying drawings of the embodiments of the present disclosure. The embodiments described hereinafter are merely part, but not all of the embodiments of the present disclosure. All other embodiments derived by those skilled in the art, based on the embodiments of the present disclosure, are within the scope of the present disclosure.

In the specification and claims of the present disclosure, the terms "first," "second," and the like are merely used to distinguish similar objects, and are not to be construed to indicate specific sequence or order. It is noted that, the data used in this way is exchangeable, such that the embodiments of the present disclosure can be implemented in the sequence other than the sequence illustrated in accompanying drawings or described herein. In addition, objects distinguished by the terms "first," "second," and the like are generally the same kind, and the terms "first," "second," and the like are not used to limit numbers of the objects. For example, a first object may be one or more. In addition, the term "and/or" in the specification and claims indicates at least one of the connected objects, and the symbol "/" generally indicates a "or" relationship between the connected objects.

The method for determining the rotation speed of the gantry in the embodiments of the present disclosure is applicable to medical equipment, such as a device for radiation therapy. The device for determining the rotation speed of the gantry is medical equipment, or an apparatus or module in the medical equipment. The medical equipment includes a gantry, a multi-leaf grating, a dosing system, and the like. The device for determining the rotation speed of the gantry performs the method for determining the rotation speed of the gantry in the embodiments of the present disclosure based on the gantry, the multi-leaf grating, the dosing system, and the like. In some embodiments, in the constant rotation of the gantry, the multi-leaf grating keeps moving to adjust a portal shape of rays, such that the device for determining the rotation speed of the gantry controls a dosing system to perform a dose radiation based on corresponding dose rate at each control point to complete therapy.

The method for determining the rotation speed of the gantry in the embodiments of the present disclosure is described hereinafter in detail by specific embodiments and application scenarios in combination with the accompanying drawings.

With the maturation of the radiation therapy technology, requirements of patients for dynamic therapy are increased, and requirements for an operation efficiency, accuracy, and stability of the dynamic therapy are increased. The existing dynamic therapy is based on a principle of an arc therapy. In the dynamic therapy, the medical equipment controls the gantry (that is, the therapy gantry), the dosing system, and the multi-leaf grating to simultaneously move to complete the therapy plan. Specifically, in the case that a start gantry angle and an end gantry angle of the therapy plan is determined, in the constant rotation of the gantry, the dosing system uniformly delivers a dose to a tumor target region, and the multi-leaf grating keeps moving to adjust a portal shape of rays.

However, the principle of the arc therapy includes the following questions in actual use. 1 How to determine a main movement shaft? That is, the medical equipment controls the gantry and the multi-leaf grating to move in accordance with the dosing system by taking the dosing system as a main movement shaft, or the medical equipment controls the dosing system and the multi-leaf grating to move in accordance with the gantry by taking the gantry as a main movement shaft. 2 How to choose an appropriate rotation speed of the gantry? As the rotation speed of the gantry is a parameter predetermined by the vendor, the rotation speed of the gantry is not accurate for different cases. Where the rotation speed of the gantry is greater, the stability of the gantry in operation is not ensured, and it is necessary to ensure that the dose rate of the dosing system is great enough to generate enough energy by the dosing system in the rotation of the gantry within one radian unit. Where the rotation speed of the gantry is less, the efficiency of the dynamic therapy is poor, such that the accuracy of performing the dynamic therapy plan is less. 3 How to achieve the cooperation operation of the gantry, the multi-leaf grating, and the dosing system? That is, in the case that the gantry rotates to an angle, whether the radiation dose of the dosing system is deviated or not, and whether the portal shape formed by the multi-leaf grating is correct or not.

To solve above technical problems, in the embodiments of the present disclosure: 1) as the gantry is required to constantly rotate in the therapy plan, and the movement range of the gantry is greater than the multi-leaf grating and the dosing system, the gantry is taken as the main movement shaft, and the multi-leaf grating and the dosing system are controlled to move in accordance with the gantry, such that the greater deviation in the rotation of the gantry is avoided, and the stability of the equipment is improved; 2) the speed required for the rotation of the gantry (that is, the rotation speed of the gantry in following embodiments) and the dose rates at the control points are determined based on leaf information and dose information of the control points, and the rotation speed of the gantry is adjusted based on the dose rates at the control points and a maximum dose rate supported by the equipment to determine the appropriate rotation speed of the gantry; 3) in dynamic therapy, the gantry is controlled constantly rotate at the determined rotation speed of the gantry, the dosing system operates with corresponding dose rates at the control points, and the leafs of the multi-leaf grating reach to positions required in the therapy plan.

In this technical solution, as the speed required for the rotation of the gantry is determined based on the therapy plan, the gantry is controlled to constantly rotate at the determined speed in dynamic therapy, so as to meet the therapy requirements. In addition, as the dose rates of the dosing system at the control points are determined based on the dose requirements at the control points, the dosing system is controlled to operate with the corresponding dose rates at the control points in dynamic therapy. As such, a data support is provided to the operation of the dynamic intensity therapy, such that the precision of the speed required for the rotation of the gantry in difference cases is improved, the requirements of dynamically adjusting the dose rates in performing the therapy plan are met, and the accuracy of performing the dynamic therapy plan is ensured.

A method for determining a rotation speed of a gantry is provided in the embodiments of the present disclosure. FIG. 1 is a flowchart of a method for determining a rotation speed of a gantry according to some embodiments of the present disclosure, and the method is applicable to a host. As shown in FIG. 1, the method for determining the rotation speed of the gantry in the embodiments of the present disclosure includes S201 to S203.

In S201, control information of the gantry is acquired.

In the embodiments of the present disclosure, the control information of the gantry includes: leaf information and dose information of control points.

In the embodiments of the present disclosure, the host acquires the leaf information and the dose information of control points, so as to determine the rotation speed of the gantry and dose rates at the control points based on the leaf information and the dose information of the control points. In addition, the host adjust the rotation speed of the gantry based on the dose rates at the control points and a maximum equipment dose rate, so as to determine a rotation speed of the gantry meeting the requirements of the equipment.

In the embodiments of the present disclosure, the host is configured to calculate related data (for example, determining the rotation speed of the gantry and the dose rates at the control points based on the control information of the gantry), and send the related data to a client, such that the client performs corresponding operations based on the data (for example, the gantry is controlled to constantly rotate based on the rotation speed of the gantry, and the dosing system is controlled to operate with corresponding dose rates at the control points).

It is noted that, as the gantry needs to rotate for an angle range in one complete dynamic therapy plan, such as half cycle (180°), one cycle (360°), or two cycles, the control point is set every predetermined included angle in the angle range in therapy plan. The therapy plan data at the control points includes gantry angles, accumulated dose values, positions of the leafs, and the like. In addition, a value of the gantry included angle between any two adjacent control points is the predetermined included angle value.

In some embodiments of the present disclosure, the predetermined included angle value is 2° or 4°. Specific value is determined based on actual use requirements, which is not limited in the embodiments of the present disclosure.

In some embodiments of the present disclosure, the leafs are the leafs in the multi-leaf grating, and the multi-leaf grating includes a plurality of leafs (such as 120).

In some embodiments of the present disclosure, the leaf information includes movement speeds of the leafs, position information of the leafs at the control points, movement displacements of the leafs from one control point to another control point, and the like. The dose information includes dose values required to be output by the dosing system at the control points (that is, dose requirements required to be met by the dosing system at the control points in the therapy plan).

In S202, the rotation speed of the gantry and dose rates at the control points are determined based on the leaf information and the dose information of the control points.

In the embodiments of the present disclosure, the host determines the rotation speed of the gantry based on the leaf information of the control points, and determines the dose rates at the control points based on the leaf information and the dose information of the control points.

In some embodiments of the present disclosure, the rotation speed of the gantry is a speed required to be applied by the gantry in the rotation (that is, the speed of the gantry to be rotated). The dose rates at the control points are dose rates required to be applied by the dosing system at the control points. It is noted that the dose rates are rates of the dosing system for outputting doses.

In S203, the rotation speed of the gantry is adjusted based on the dose rates at the control points and a maximum equipment dose rate.

In the embodiments of the present disclosure, the maximum equipment dose rate is a maximum dose rate supported by the equipment corresponding to the dosing system. It is noted that the equipment corresponding to the dosing system is equipment including the dosing system, that is, equipment where the dosing system is.

In some embodiments of the present disclosure, the host determines whether to adjust the rotation speed of the gantry based on the dose rates at the control points and the maximum equipment dose rate. Where the dose rates at the control points include a dose rate greater than the maximum equipment dose rate, the rotation speed of the gantry is adjusted based on the dose information corresponding to the maximum equipment dose rate (for example, a difference value between dose values of two adjacent control points corresponding to the maximum dose rate at the control point) and the maximum equipment dose rate. Where the dose rates at the control points are less than or equal to the maximum equipment dose rate, the rotation speed of the gantry is not adjusted.

It is understood that the rotation speed of the gantry meeting the requirements of the equipment is determined by adjusting the rotation speed of the gantry, such that the gantry is controlled to constantly rotate with the rotation speed of the gantry in therapy to complete therapy.

A method for determining a rotation speed of a gantry is provided in the embodiments of the present disclosure, the leaf information and the dose information of control points are acquired, such that the rotation speed of the gantry and the dose rates at the control points are determined based on the leaf information and the dose information of the control points. In addition, the rotation speed of the gantry is adjusted based on the dose rates at the control points and the maximum equipment dose rate. In the solutions, the speed required to rotate the gantry (that is, the rotation speed of the gantry) and the dose rates of the dosing system at the control points are determined based on the therapy plan, and the rotation speed of the gantry is adjusted based on the dose rates at the control points, so as to determine an appropriate rotation speed of the gantry. On this basis, in dynamic therapy, the gantry is controlled to constantly rotate with the determined rotation speed of the gantry, and the dosing system is controlled to operate with the corresponding dose rates at the control points. As such, a data support is provided to the operation of the dynamic intensity therapy, the precision of the speed required for the rotation of the gantry in difference cases is improved, and the accuracy of performing the dynamic therapy plan is ensured.

Figure 2:
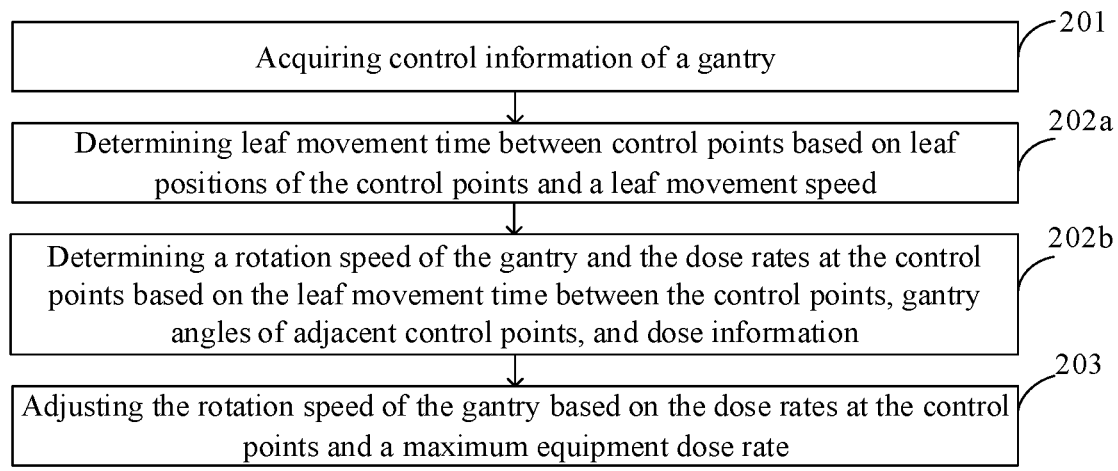
FIG. 2 is a flowchart of another method for determining a rotation speed of a gantry according to some embodiments of the present disclosure.

In some embodiments of the present disclosure, in conjunction with FIG. 1, as shown in FIG. 2, the leaf information includes leafs positions of the control points and the leaf movement speed. Specifically, S202 is performed by following S202a and S202b.

In S202a, leaf movement time between the control points is determined based on the leaf positions of the control points and the leaf movement speed.

In some embodiments of the present disclosure, the leaf positions of the control points are desired positions of the leafs in therapy plan. In the case that the leafs rotate to the desired positions in therapy plan at the control points, a portal shape of rays matches with a shape of the tumor target region.

In some embodiments of the present disclosure, the leaf movement speed is a constant values related to property parameters of the equipment corresponding to the leafs. For example, the leaf movement speed is 2.5 cm/s. It is noted that the equipment corresponding to the leafs is the equipment including the leafs, that is, the equipment where the leafs are.

In some embodiments of the present disclosure, the leaf movement time is a duration required by the leaf to move from a position of the leaf at one control point to a position of the leaf at another control point adjacent to the one control point.

In some embodiments of the present disclosure, for any control point (such as, a first control point), the host determines the leaf movement time based on a position of a leaf at the first control point and a position of a leaf at a control point adjacent to the first control point (such as, a second control point).

It is noted that the embodiments of the present disclosure are described by taking one leaf of the multi-leaf grating as an example, and any leaf of the multi-leaf grating at any control point may implement the solutions in the embodiments of the present disclosure.

In some embodiments of the present disclosure, specifically, S202a is performed by following S202a1 and S202a2.

In S202a1, leaf movement displacements between the adjacent control points are calculated based on the leaf positions of the control points.

In some embodiments of the present disclosure, for any control point (such as, a first control point), the host determines a leaf movement displacement between the first control point and the second control point based on the position of the leaf at the first control point and the position of the leaf at the control point adjacent to the first control point (such as, the second control point).

It is noted that the method for determining the leaf movement displacements between the adjacent control points is implemented in the embodiments of the present disclosure. In some embodiments, the host determines a leaf movement displacement between the second control point and a third control point based on the position of the leaf at the second control point and a position of the leaf at the third control point. The third control point is a control point adjacent to the second control point.

In S202a2, the leaf movement time between the control points is determined based on the leaf movement displacements between the adjacent control points and the leaf movement speed.

In some embodiments of the present disclosure, upon determining all leaf movement displacements between the adjacent control points, the host determines a maximum leaf movement displacement using a first predetermined algorithm. In some embodiments, the first predetermined algorithm is MaxL=Max (MLC$_{[N+1][I]}$−MLC$_{[N][I]}$).

MLC$_{[N+1][I]}$ represents a position of $I^{th}$ leaf at $(N+1)^{th}$ control point, MLC$_{[N][I]}$ represents a position of $I^{th}$ leaf at $N^{th}$ control point, MaxL represents a maximum leaf movement displacement in therapy, and both N and I are positive integers.

In some embodiments of the present disclosure, the host determines a first displacement based on the position of the leaf at the first control point and the position of the leaf at the second control point, determines a second displacement based on the position of the leaf at the second control point and a position of a leaf at a third control point. . . . Upon determining at least one displacement, the host determines a maximum leaf movement displacement from the at least one displacement, and then determines the leaf movement time based on the maximum leaf movement displacement and the leaf movement speed. The leaf movement time is a maximum leaf movement time.

In some embodiments, it is noted that the host calculates a plurality of displacements based on the positions of the leafs between two adjacent control points. Then, the host selects a maximum displacement from the plurality of displacements as the maximum leaf movement displacement.

In some embodiments of the present disclosure, the host determines the leaf movement time based on the maximum leaf movement displacement and the leaf movement speed using a second predetermined algorithm. In some embodiments, the second predetermined algorithm is $$\text{Max } T = \frac{\text{Max } L}{MLCS}.$$

MLCS represents the leaf movement speed, MaxT represents the leaf movement time, that is, a maximum duration required by the leaf to move. It is acquired based on the second predetermined algorithm that the leaf movement time is negatively correlated with the leaf movement speed, and is positively correlated with the maximum leaf movement displacement.

In some embodiments of the present disclosure, the maximum duration required by the leaf to move is determined by determining the maximum leaf movement displacement. As such, the leafs of the multi-leaf grating at the control points have enough time to reach to positions required in the therapy plan in dynamic therapy, so as to ensure the accuracy of performing the dynamic therapy plan.

In S202b, the rotation speed of the gantry and the dose rates at the control points are determined based on the leaf movement time between the control points, gantry angles of adjacent control points, and the dose information.

In some embodiments of the present disclosure, specifically, S202b is performed by following S202b1 and S202b2.

In S202b1, the rotation speed of the gantry is determined based on the leaf movement time between the control points and the gantry angles of adjacent control points.

In some embodiments of the present disclosure, the host determines the rotation speed of the gantry based on the maximum leaf movement time and the gantry angles of adjacent control points using a fourth predetermined algorithm. In some embodiments, the fourth predetermined algorithm is $$GS_1 = \frac{\Delta D}{\text{Max } T}.$$

$\Delta D$ represents the gantry angle of two adjacent control points, $GS_1$ represents the speed required by the gantry to rotate (that is, the rotation speed of the gantry). It is acquired based on the fourth predetermined algorithm that the rotation speed of the gantry negatively correlated with the leaf movement time (that is, the maximum leaf movement time), and is positively correlated with the gantry angle of two adjacent control points.

In some embodiments of the present disclosure, in the entire dynamic therapy, the host controls the gantry to constantly rotate with a speed less than or equal to the rotation speed of the gantry, such that the leafs at the control points have enough time to reach to positions required in the therapy plan in dynamic therapy.

In some embodiments of the present disclosure, as the gantry is required to constantly rotate in the therapy plan, and the movement range of the gantry is greater than the multi-leaf grating and the dosing system, the gantry is taken as the main movement shaft, and the multi-leaf grating and the dosing system are controlled to move in accordance with the gantry, such that the greater deviation in the movement of the gantry is avoided, and the stability of the equipment is ensured.

In S202b2, the dose rates at the control points are determined based on the leaf movement time between the control points and the dose information.

In some embodiments of the present disclosure, for any control point (such as, the first control point), the host determines a dose rate at the first control point based on a difference value of a dose value at the first control point and a dose value at a control point adjacent to the first control point (such as, the second control point) and the leaf movement time.

In some embodiments of the present disclosure, the host determines the dose rate at the first control point based on a difference value of a dose value at the second control point and a dose value at the first control point and the leaf movement time using a third predetermined algorithm. In some embodiments, the third predetermined algorithm is $$DR_N = \frac{Dose_{N+1} - Dose_N}{Max\ T}.$$

$Dose_{N+1}$ represents a dose value required to be output by the dosing system at the $(N+1)^{th}$ control point, $Dose_N$ represents a dose value required to be output by the dosing system at the $N^{th}$ control point, and $DR_N$ represents a dose rate at $N^{th}$ control point.

It is noted that, as at least one control point is set in the therapy plan, for each control point in the at least one control point, the host determines the dose rate at each control point in the embodiments of the present disclosure. The dosing system is controlled to operate based on corresponding dose rate at each control point to complete therapy. For example, the host determines the dose rate at the second control point based on the leaf movement time and one difference value of dose values (a difference value of a dose value at the third control point and a dose value at the second control point).

In some embodiments of the present disclosure, after the rotation speed of the gantry and the dose rates at the control points are determined, the gantry is controlled to constantly rotate based on the rotation speed of the gantry. In addition, the dosing system is controlled to perform a dose radiation based on corresponding dose rate at each control point to complete therapy.

It is noted that, after the rotation speed of the gantry is determined, whether the rotation speed of the gantry is less than or equal to a maximum rotation speed supported by the equipment is determined to determine whether the equipment of the gantry is capable of operating with the rotation speed of the gantry. Specifically, the gantry is controlled, in response to the rotation speed of the gantry being less than or equal to the maximum rotation speed supported by the equipment, to rotate based on the rotation speed of the gantry. The gantry is controlled, in response to the rotation speed of the gantry being greater than the maximum rotation speed supported by the equipment, to rotate based on the maximum rotation speed supported by the equipment, and the dose rates of the dosing system at the control points are determined again.

In some embodiments of the present disclosure, for any control point (such as, the first control point), the leaf movement time is determined again based on the maximum rotation speed supported by the equipment and the gantry angles of adjacent control points. Then, the dose rate at the first control point is determined again based on the leaf movement time of the leaf, a dose value of the first control point and a difference value of dose values of the first control point and the adjacent control point (such as the second control point). In dynamic therapy, the dosing system is controlled to operate at the control point based on the dose rate to complete therapy.

In the embodiments of the present disclosure, as the speed required to rotate the gantry is determined based on the therapy plan, a data support is provided to the operation of the dynamic intensity therapy. Thus, the gantry is controlled to constantly rotate at the determined speed in dynamic therapy, so as to meet the therapy requirements and ensure the accuracy of performing the dynamic therapy plan.

Figure 3:
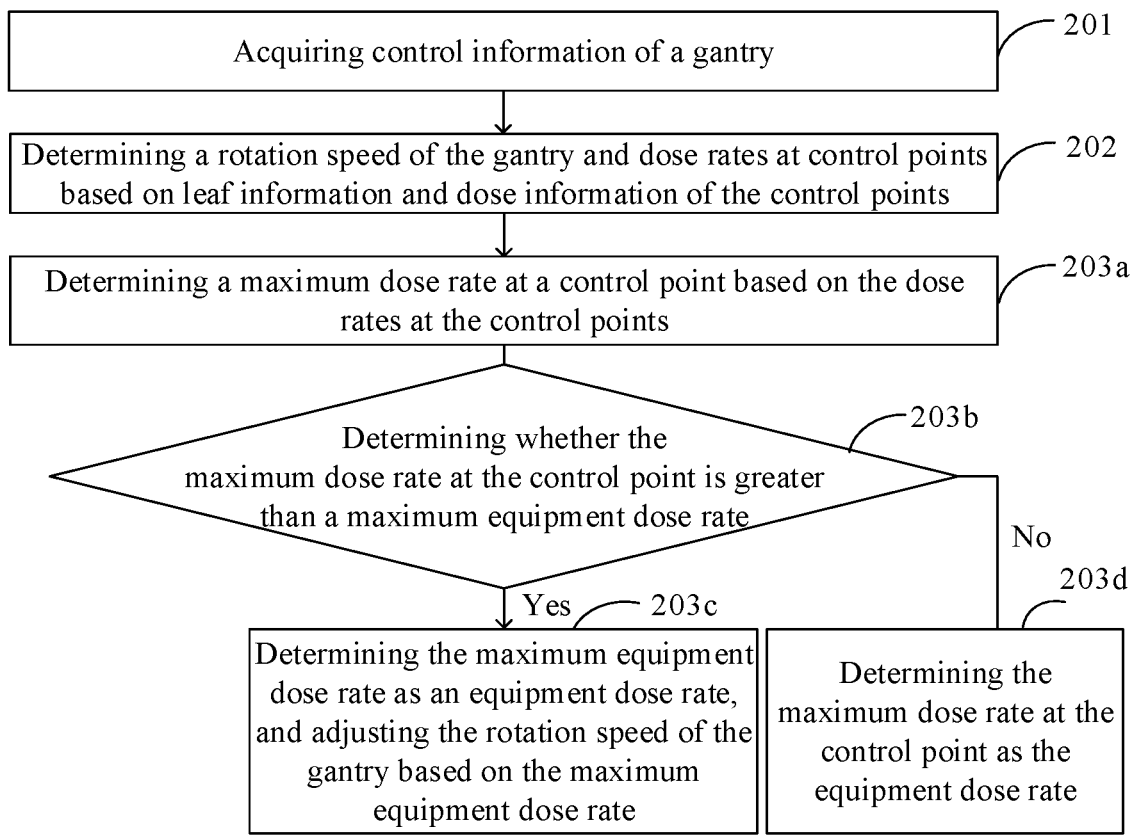
FIG. 3 is a flowchart of another method for determining a rotation speed of a gantry according to some embodiments of the present disclosure.

In some embodiments of the present disclosure, in conjunction with FIG. 1, as shown in FIG. 3, S203 is performed by following S203a and S203c (or S203d).

In S203a, a maximum dose rate at a control point is determined based on the dose rates at the control points.

In some embodiments of the present disclosure, after the dose rates at the control points are determined, the host determines the maximum dose rate from the dose rates as the maximum dose rate at the control point. That is, the maximum dose rate at the control point is a maximum dose rate in the dose rates at the control points.

In S203b, whether the maximum dose rate at the control point is greater than a maximum equipment dose rate is determined.

In S203c, the maximum equipment dose rate is determined, in response to the maximum dose rate at the control point being greater than the maximum equipment dose rate, as an equipment dose rate, and the rotation speed of the gantry is adjusted based on the maximum equipment dose rate.

In some embodiments of the present disclosure, the equipment dose rate is a dose rate required by the dosing system in therapy. It is noted that, as the equipment dose rate is determined, in response to the maximum dose rate at the control point being greater than the maximum equipment dose rate, as the maximum equipment dose rate, the dosing system is controlled to operate with the maximum equipment dose rate in dynamic therapy. It is noted that, determining the maximum equipment dose rate as the equipment dose rate indicates that the maximum equipment dose rate is taken as the equipment dose rate.

In some embodiments of the present disclosure, the dosing system is controlled to operate at the control point at which the dose rate is greater than the maximum equipment dose rate. Specifically, whether the dose rates at the control points are greater than the maximum equipment dose rate is determined, and the dosing system is controlled, in response to a dose rate at a control point being greater than the maximum equipment dose rate, to operate at the control point with the maximum equipment dose rate. In some embodiments, the dosing system is controlled, in response to the dose rate at the first control point being greater than the maximum equipment dose rate, to operate at the first control point with the maximum equipment dose rate.

In some embodiments of the present disclosure, in the case that the maximum dose rate at the control point is greater than the maximum equipment dose rate, the speed required to rotate the gantry is determined again. That is, the speed required to rotate the gantry is reduced to prolong the operation time of the gantry. As such, the gantry is controlled to constantly rotate based on the determined rotation speed in dynamic therapy, and the dosing system is controlled to perform the dose radiation based on the maximum equipment dose rate at the control point at which the dose rate is greater than the maximum equipment dose rate, so as to complete therapy.

In the embodiments of the present disclosure, after the dose rates at the control points are determined, whether the dose rates are less than or equal to the maximum dose rate supported by the equipment is determined, so as to determine whether the equipment of the dosing system is capable of operating with the dose rate. As such, the dose rates at the control points supported by the equipment are determined based on the therapy plan, such that the requirements of adjusting the dose rates are met in the therapy plan, and the accuracy of performing the dynamic therapy plan is ensured.

In some embodiments of the present disclosure, "determining the rotation speed of the gantry based on the maximum rotation speed of the gantry of the equipment" in S203c is performed by following S203c1 and S203c2.

In S203c1, movement time of the dosing system is determined based on a difference value between dose values of two adjacent control points corresponding to the maximum dose rate at the control point and the maximum equipment dose rate.

In some embodiments of the present disclosure, the host calculates the rotation speed of the gantry based on maximum dose rate supported by the equipment.

Specifically, the host determines the movement time of the dosing system based on the difference value between dose values of two adjacent control points corresponding to the maximum dose rate at the control point and the maximum equipment dose rate using a fifth predetermined algorithm. In some embodiments, the fifth predetermined argorithm is $$T_N = \frac{\text{Dose}_{N:1} - \text{Dose}_N}{DR_{Max}}.$$

$T_N$ represents time at the $N^{th}$ control point required by the movement of the dosing system (that is, the movement time of the dosing system). Then, the host again determines the speed required to rotate the gantry based on based on the movement time of the dosing system and the gantry angles of the adjacent control points, and adjusts the rotation speed of the gantry to the target rotation speed. It is required from the fifth predetermined algorithm that, the movement time of the dosing system is negatively correlated with the maximum dose rate at the control point, and is positively correlated with the difference value between dose values of two control points adjacent to the control point.

In S203c1, a target rotation speed is determined based on the movement time of the dosing system and the gantry angles of the adjacent control points, and the rotation speed of the gantry is adjusted to the target rotation speed.

In some embodiments of the present disclosure, the host determines the target rotation speed based on the movement time of the dosing system and the gantry angles of the adjacent control points using a sixth predetermined algorithm. In some embodiments, the sixth predetermined algorithm is $$GS_2 = \frac{\Delta D}{T_N}.$$

$\Delta D$ represents the gantry angles of the adjacent control points, $GS_2$ represents a speed required to rotate the gantry (that is, the target rotation speed). It is required from the sixth predetermined algorithm that, the target rotation speed is negatively correlated with the movement time of the dosing system, and is positively correlated with the gantry angles of the adjacent control points.

In the embodiments of the present disclosure, it is required from the third predetermined algorithm and the fifth predetermined algorithm that the movement time $T_N$ of the dosing system is greater than the maximum duration MaxT required by the leaf to move. Thus, the target rotation speed $GS_2$ is less than the rotation speed of the gantry $GS_1$. As such, the rotation speed of the gantry $GS_1$ is reduced to the target rotation speed $GS_2$, so as to reduce the rotation speed of the gantry.

In some embodiments of the present disclosure, the host determines the dose rates at the control points according to above embodiments. In the case that a dose rate at a control point being greater than the maximum dose rate supported by the equipment, the speed required to rotate the gantry is determined again. As such, after the speeds required to rotate the gantry at the control points are determined, the host selects a minimum rotation speed from the speeds and takes the minimum rotation speed as the rotation speed of the gantry in dynamic therapy, so as to determine the speed in dynamic therapy.

In the embodiments of the present disclosure, in the case that a dose rate at a control point is greater than the maximum dose rate supported by the equipment, the speed required to rotate the gantry is determined again. That is, in the case that the movement time of the leafs in the multi-leaf grating meets the therapy plan, it is necessary to ensure that the dose rates of the dosing system at the control points meet the requirements, such that the accuracy of performing the dynamic therapy plan is ensured.

In S203d, the maximum dose rate at the control point is determined, in response to the maximum dose rate at the control point being less than or equal to the maximum equipment dose rate, as the equipment dose rate.

It is noted that, in the case that the maximum dose rate at the control point is less than or equal to the maximum equipment dose rate, the dose rates at the control points are less than or equal to the maximum equipment dose rate. Thus, in dynamic therapy, the maximum dose rate at the control point is taken as the equipment dose rate, and the dosing system is controlled to operate with the maximum dose rate at the control point at the control point corresponding to the maximum dose rate at the control point.

In some embodiments of the present disclosure, the dosing system is controlled to operate based on corresponding dose rate at the control point at which the dose rate is less than or equal to the maximum equipment dose rate. Specifically, whether the dose rates at the control points are less than or equal to the maximum equipment dose rate is determined. The dosing system is controlled, in response to a dose rate at a control point being less than or equal to the maximum equipment dose rate, to operate based on corresponding dose rate at the control point. In some embodiments, the dosing system is controlled, in response to the dose rate at the first control point being less than the maximum equipment dose rate, to operate based on corresponding dose rate at the first control point.

In the embodiments of the present disclosure, after the dose rates at the control points are determined, whether the dose rates at the control points are less than or equal to the maximum dose rate supported by the equipment is determined. In the case that the dose rates are less than or equal to the maximum dose rate supported by the equipment, the dose rates at the control points are effective dose rates. Thus, the dosing system is controlled to perform the therapy based on corresponding dose rates at the control points in dynamic therapy. As such, the requirements of adjusting the dose rates in performing the therapy plan are met, and the accuracy of performing the dynamic therapy plan is ensured.

It is noted that, in the method for determining the rotation speed of the gantry in the embodiments of the present disclosure, the performing body is an apparatus for determining a rotation speed of a gantry, medical equipment, or a controlling module used to performing the method for determining the rotation speed of the gantry in the apparatus for determining the rotation speed of the gantry. The embodiments of the present disclosure illustrative the apparatus for determining the rotation speed of the gantry in the embodiments of the present disclosure by taking the apparatus for determining the rotation speed of the gantry performing the method for determining the rotation speed of the gantry as an example.

Figure 4:
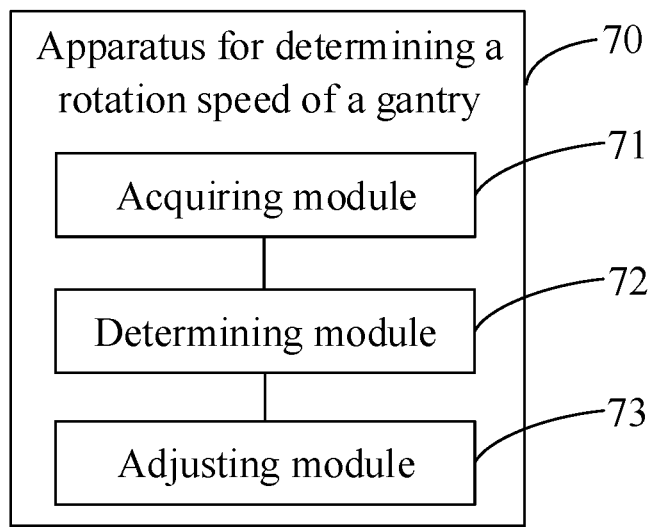
FIG. 4 is a schematic structural diagram of an apparatus for determining a rotation speed of a gantry according to some embodiments of the present disclosure.

FIG. 4 is a schematic structural diagram of an apparatus for determining a rotation speed of a gantry according to some embodiments of the present disclosure. As shown in FIG. 4, the apparatus 70 for determining the rotation speed of the gantry includes an acquiring module 71, a determining module 72, and an adjusting module 73.

The acquiring module 71 is configured to acquire control information of the gantry, wherein the control information of the gantry includes: leaf information and dose information of control points. The determining module 72 is configured to determine the rotation speed of the gantry and dose rates at the control points based on the leaf information and the dose information of the control points. The adjusting module 73 is configured to adjust the rotation speed of the gantry based on the dose rates at the control points and a maximum equipment dose rate.

An apparatus for determining a rotation speed of a gantry is provided in the embodiments of the present disclosure. In the apparatus, the speed required to rotate the gantry (that is, the rotation speed of the gantry) and the dose rates of the dosing system at the control points are determined based on the therapy plan, and the rotation speed of the gantry is adjusted based on the dose rates at the control points, so as to determine an appropriate rotation speed of the gantry. Thus, in dynamic therapy, the gantry is controlled to constantly rotate with the determined rotation speed of the gantry, and the dosing system is controlled to operate with the corresponding dose rates at the control points. As such, a data support is provided to the operation of the dynamic intensity therapy, the precision of the speed required for the rotation of the gantry in difference cases is improved, and the accuracy of performing the dynamic therapy plan is ensured.

In some embodiments of the present disclosure, the leaf information includes: leaf positions of the control points and a leaf movement speed. The determining module 72 is further configured to: determine leaf movement time between the control points based on the leaf positions of the control points and the leaf movement speed; and determine the rotation speed of the gantry and the dose rates at the control points based on the leaf movement time between the control points, gantry angles of adjacent control points, and the dose information.

In some embodiments of the present disclosure, the determining module 72 is further configured to: calculate, based on the leaf positions of the control points, leaf movement displacements between the adjacent control points; and determine the leaf movement time between the control points based on the leaf movement displacements between the adjacent control points and the leaf movement speed.

In some embodiments of the present disclosure, the determining module 72 is further configured to: determine a maximum leaf movement displacement from the leaf movement displacements between the adjacent control points; and determine the leaf movement time between the control points based on the maximum leaf movement displacement and the leaf movement speed, wherein the leaf movement time is positively correlated with the maximum leaf movement displacements, and is negatively correlated with the leaf movement speed.

In some embodiments of the present disclosure, the determining module 72 is further configured to: determine the rotation speed of the gantry based on the leaf movement time between the control points and the gantry angles of adjacent control points; and determine the dose rates at the control points based on the leaf movement time between the control points and the dose information.

In some embodiments of the present disclosure, the dose information of the control points includes dose values required to be output by a dosing system at the control points; the dose rate at first control point in the control points is negatively correlated with the leaf movement time, and is positively correlated with difference values of dose values, wherein the difference values of dose values are difference values between dose values of the first control points and dose values of the adjacent control points; and the rotation speed of the gantry is negatively correlated with the leaf movement time, and is positively correlated with the gantry angles of the adjacent control points.

In some embodiments of the present disclosure, the adjusting module 73 is further configured to: determine a maximum dose rate at a control point based on the dose rates at the control points; determine, in response to the maximum dose rate at the control point being greater than the maximum equipment dose rate, the maximum equipment dose rate as an equipment dose rate, and adjust the rotation speed of the gantry based on the maximum equipment dose rate; and determine, in response to the maximum dose rate at the control point being less than or equal to the maximum equipment dose rate, the maximum dose rate at the control point as the equipment dose rate.

In some embodiments of the present disclosure, the adjusting module 73 is further configured to: not adjust the rotation speed of the gantry in response to the maximum dose rate at the control point being less than or equal to the maximum equipment dose rate.

In some embodiments of the present disclosure, the adjusting module 73 is further configured to: determine movement time of the dosing system based on a difference value between dose values of two adjacent control points corresponding to the maximum dose rate at the control point and the maximum equipment dose rate; and determine a target rotation speed based on the movement time of the dosing system and the gantry angles of the adjacent control points, and adjust the rotation speed of the gantry to the target rotation speed.

In some embodiments of the present disclosure, the movement time of the dosing system is negatively correlated with the maximum equipment dose rate, and is positively correlated with the difference value between the dose values of two adjacent control points corresponding to the maximum dose rate at the control point; and the target rotation speed is negatively correlated with the movement time of the dosing system, and is positively correlated with the gantry angles of the adjacent control points.

In some embodiments, the apparatus for determining the rotation speed of the gantry is a device, or parts, integrated circuits, or chips in the medical equipment. The device is a mobile electronic device, or a non-mobile electronic device.

The apparatus for determining the rotation speed of the gantry in the embodiments of the present disclosure may achieves processes in above method embodiments, and has the same technical effects, and thus, is not described in detail herein.

Figure 5:
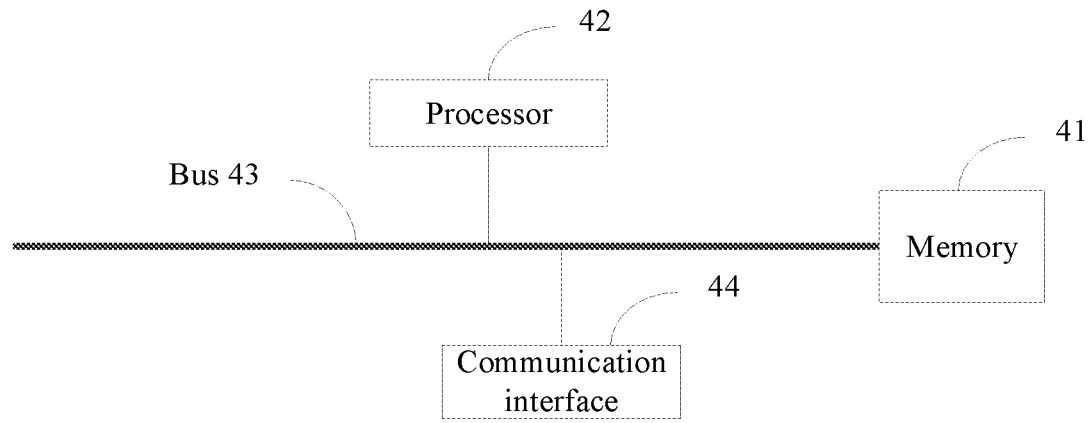
FIG. 5 is a schematic diagram of a hardware structure of medical equipment according to some embodiments of the present disclosure.

FIG. 5 is a schematic diagram of a hardware structure of medical equipment according to some embodiments of the present disclosure. The medical equipment includes a memory 41, a processor 42, a bus 43, and a communication interface 44. The memory 41 is configured to store computer-executable instructions, and the processor 42 is connected to the memory 41 by the bus 43. In the case that the medical equipment operates, the processor 42, when loading and executing the computer-executable instructions stored in the memory 41, causes the medical equipment to perform the method for determining the rotation speed of the gantry in above embodiments.

Figure 6:
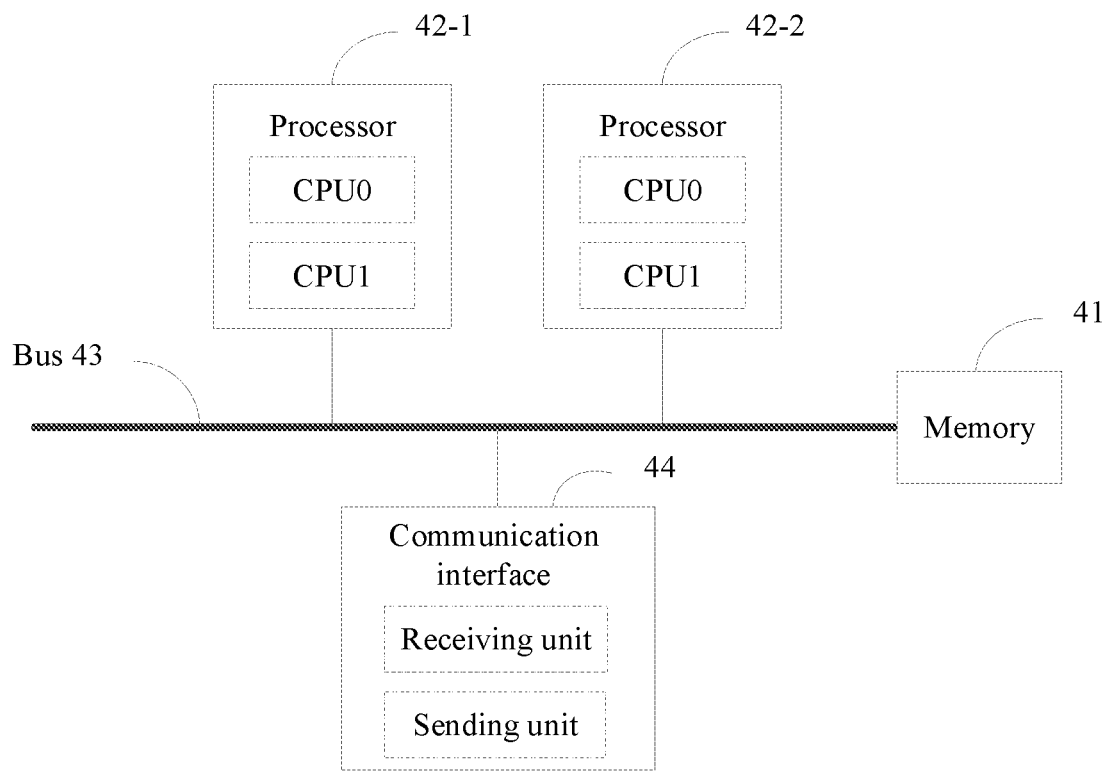
FIG. 6 is a schematic diagram of another hardware structure of medical equipment according to some embodiments of the present disclosure.

In some embodiments, in conjunction with FIG. 5, as shown in FIG. 6, the processor 41 (42-1 and 42-2) includes one or more central processing units (CPU), such as CPU0 and CPU1 in FIG. 6. In some embodiments, the medical equipment includes a plurality of processors 41, such as the processor 42-1 and the processor 42-2 in FIG. 6. In some embodiments, the CPU in the processor 42 is a single-CPU, or a multi-CPU. In some embodiments, the processor 42-2 is one or more devices, circuits, and/or processor cores for processing data (such as the computer-executable instructions).

In some embodiments, the memory 41 is a read-only memory (ROM) 41 or other static memory used to store static information and instructions, random access memory (RAM) or other dynamic memory used to store static information and instructions, electrically erasable programmable read-only memory (EEPROM), compact disc read-only memory (CD-ROM) or other compact disc memory, disc memory (such as, compact disc, laser disc, optical disc, digital versatile disc, and Blu-ray disc), magnetic disk storage media or other magnetic disk storage media, or any media that carries or stores program codes including instructions or data structures and is accessed by the computer, but is not limited in this. In some embodiments, the memory 41 is alone, and is connected to the processor 42 by the bus 43. In some embodiments, the memory 41 is integrated with the processor 42.

In some embodiments, the memory 41 is configured to store data in the embodiments of the present disclosure and perform computer-executable instructions corresponding to the software programs in the embodiments of the present disclosure. In some embodiments, the processor 42 achieves various functions of the medical equipment by executing or performing the software programs in the memory 41 and calling the data in the memory 41.

In some embodiments, the communication interface 44 uses devices such as transceiver, and is configured to communicate with other devices or communication network, such as a control system, a radio access network (RAN), a wireless local area networks (WLAN), or the like. In some embodiments, the communication interface 44 includes: a receiving unit to implement a receiving function, and a sending unit to implement a sending function.

In some embodiments, the bus 43 is an industry standard architecture (ISA) bus, a peripheral component interconnect (PCI) bus, an extended industry standard architecture (EISA) bus, and the like. In some embodiments, the bus 43 includes an address bus, a data bus, a control bus, and the like. For convenience, FIG. 6 shows one thick line, which does not indicate only one or one kind bus.

It is noted that, the apparatus for determining the rotation speed of the gantry in the embodiments of the present disclosure is also implemented by the structure in FIG. 5 or FIG. 6.

In the embodiments of the present disclosure, a readable storage medium is further provided. The readable storage medium stores one or more programs or instructions, wherein the one or more programs or instructions, when loaded and executed by a processor, cause the processor to perform processes in the method for determining the rotation speed of the gantry. In addition, the same technical effects are achieved, and thus, are not described in detail herein.

The processor is the processor in the medical equipment in above embodiments. The readable storage medium includes a computer-readable storage medium, for example, a read-only memory (ROM), a random-access memory (RAM), a disk, a disc, or the like.

A chip is provided in the embodiments of the present disclosure. The chip includes a processor and a communication interface, wherein the communication interface is coupled to the processor, and the processor, when loading and executing one or more programs or instructions, is caused to perform processes in the method for determining the rotation speed of the gantry. In addition, the same technical effects are achieved, and thus, are not described in detail herein.

The chip in the embodiments of the present disclosure is also referred to as a system-on-chip, a system chip, a chip system, a system on chip, or the like.

A computer program product is provided in the embodiments of the present disclosure. The computer program product includes one or more instructions, wherein a processor, when loading and executing the one or more instructions, is caused to perform processes in the method for determining the rotation speed of the gantry. In addition, the same technical effects are achieved, and thus, are not described in detail herein.

It should be noted that, the terms "comprise," "include," or any other variation herein are intended to cover non-exclusive inclusion, such that a process, method, article or device comprising a series of elements includes those elements and other elements not expressly listed or inherent elements in such process, method, article or apparatus. Without further limitation, an element limited by the phrase "comprising one . . . " does not preclude the presence of other identical elements in the process, method, article or apparatus that includes the element. Furthermore, it should be noted that the scope of the method and apparatus in the embodiments of the present application is not limited to performing the functions in the order shown or discussed, and may also include performing the functions in a substantially simultaneous manner or in the reverse order based on the functions. For example, the method may be performed in an order different from that described, and various steps may also be added, omitted, or combined. In addition, features described with reference to some embodiments may be combined in other embodiments.

By the description in above embodiments, those skilled in the art can clearly understand that above embodiment method can be achieved by software and necessary general hardware platform, or hardware, but the former is better. On this basis, the nature or a part, contributing to the prior art, of the technical solutions of the present disclosure are described in the form of computer software products. The computer software product is stored in a storage medium (for example, a ROM/RAM, a magnetic disk, or an optical disc), and includes several instructions to cause a terminal (for example, a mobile phone, a computer, a server, a network device, or the like) to execute the method in the embodiments of the present disclosure.

The embodiments of the present disclosure are described above in conjunction with the accompany drawings, and are limited the above embodiments. Above embodiments are exemplary, and are not limiting. With the inspiration of the present disclosure, those of ordinary skill in the art can derive many forms without departing from the purpose of the present disclosure and the scope of protection of and the claims, which all belong to the protection of the present disclosure.

What is claimed is:

1. A method for determining a rotation speed of a gantry, comprising:
    acquiring control information of the gantry, wherein the control information of the gantry comprises leaf information and dose information of control points;
    determining the rotation speed of the gantry and dose rates at the control points based on the leaf information and the dose information of the control points; and
    adjusting the rotation speed of the gantry based on the dose rates at the control points and a maximum equipment dose rate.

2. The method according to claim 1, wherein
    the leaf information comprises: leaf positions of the control points and a leaf movement speed; and
    determining the rotation speed of the gantry and the dose rates at the control points based on the leaf information and the dose information of the control points comprises:
        determining leaf movement time between the control points based on the leaf positions of the control points and the leaf movement speed; and
        determining the rotation speed of the gantry and the dose rates at the control points based on the leaf movement time between the control points, gantry angles of adjacent control points, and the dose information.

3. The method according to claim 2, wherein determining the leaf movement time between the control points based on the leaf positions of the control points and the leaf movement speed comprises:
    calculating, based on the leaf positions of the control points, leaf movement displacements between the adjacent control points; and
    determining the leaf movement time between the control points based on the leaf movement displacements between the adjacent control points and the leaf movement speed.

4. The method according to claim 3, wherein determining the leaf movement time between the control points based on the leaf movement displacements between the adjacent control points and the leaf movement speed comprises:
    determining a maximum leaf movement displacement from the leaf movement displacements between the adjacent control points; and
    determining the leaf movement time between the control points based on the maximum leaf movement displacement and the leaf movement speed, wherein the leaf movement time is positively correlated with the maximum leaf movement displacements, and is negatively correlated with the leaf movement speed.

5. The method according to claim 2, wherein determining the rotation speed of the gantry and the dose rates at the control points based on the leaf movement time between the control points, the gantry angles of adjacent control points, and the dose information comprises:
    determining the rotation speed of the gantry based on the leaf movement time between the control points and the gantry angles of adjacent control points; and
    determining the dose rates at the control points based on the leaf movement time between the control points and the dose information.

6. The method according to claim 5, wherein
    the dose information of the control points comprises dose values required to be output by a dosing system at the control points;
    a dose rate at a first control point in the control points is negatively correlated with the leaf movement time, and is positively correlated with difference values of dose values, wherein the difference values of dose values are difference values between dose value of the first control point and dose values of the adjacent control points; and
    the rotation speed of the gantry is negatively correlated with the leaf movement time, and is positively correlated with the gantry angles of the adjacent control points.

7. The method according to claim 1, wherein adjusting the rotation speed of the gantry based on the dose rates at the control points and the maximum equipment dose rate comprises:
    determining a maximum dose rate at a control point based on the dose rates at the control points; and
    determining, in response to the maximum dose rate at the control point being greater than the maximum equipment dose rate, the maximum equipment dose rate as an equipment dose rate, and adjusting the rotation speed of the gantry based on the maximum equipment dose rate.

8. The method according to claim 7, further comprising:
    determining, in response to the maximum dose rate at the control point being less than or equal to the maximum equipment dose rate, the maximum dose rate at the control point as the equipment dose rate.

9. The method according to claim 8, further comprising:
    not adjusting the rotation speed of the gantry in response to the maximum dose rate at the control point being less than or equal to the maximum equipment dose rate.

10. The method according to claim 7, wherein adjusting the rotation speed of the gantry based on the maximum equipment dose rate comprises:
    determining movement time of the dosing system based on a difference value between dose values of two adjacent control points corresponding to the maximum dose rate at the control point and the maximum equipment dose rate; and
    determining a target rotation speed based on the movement time of the dosing system and the gantry angles of the adjacent control points, and adjusting the rotation speed of the gantry to the target rotation speed.

11. The method according to claim 10, wherein
    the movement time of the dosing system is negatively correlated with the maximum equipment dose rate, and is positively correlated with the difference value between the dose values of two adjacent control points corresponding to the maximum dose rate at the control point; and
    the target rotation speed is negatively correlated with the movement time of the dosing system, and is positively correlated with the gantry angles of the adjacent control points.

12. A device for determining a rotation speed of a gantry, comprising: a processor, a memory, and one or more programs or instructions stored on the memory and executable on the processor, wherein the processor, when loading and executing the one or more programs or instructions, is caused to perform a method for determining a rotation speed of a gantry comprising:
acquiring control information of the gantry, wherein the control information of the gantry comprises: leaf information and dose information of control points;
determining the rotation speed of the gantry and dose rates at the control points based on the leaf information and the dose information of the control points; and
adjusting the rotation speed of the gantry based on the dose rates at the control points and a maximum equipment dose rate.

13. The device according to claim 12, wherein the leaf information comprises: leaf positions of the control points and a leaf movement speed; and determining the rotation speed of the gantry and the dose rates at the control points based on the leaf information and the dose information of the control points comprises:
determining leaf movement time between the control points based on the leaf positions of the control points and the leaf movement speed; and
determining the rotation speed of the gantry and the dose rates at the control points based on the leaf movement time between the control points, gantry angles of adjacent control points, and the dose information.

14. The device according to claim 13, wherein determining the leaf movement time between the control points based on the leaf positions of the control points and the leaf movement speed comprises:
calculating, based on the leaf positions of the control points, leaf movement displacements between the adjacent control points; and
determining the leaf movement time between the control points based on the leaf movement displacements between the adjacent control points and the leaf movement speed.

15. The device according to claim 13, wherein determining the rotation speed of the gantry and the dose rates at the control points based on the leaf movement time between the control points, the gantry angles of adjacent control points, and the dose information comprises:
determining the rotation speed of the gantry based on the leaf movement time between the control points and the gantry angles of adjacent control points; and
determining the dose rates at the control points based on the leaf movement time between the control points and the dose information.

16. The device according to claim 12, wherein adjusting the rotation speed of the gantry based on the dose rates at the control points and the maximum equipment dose rate comprises:
determining a maximum dose rate at a control point based on the dose rates at the control points; and
determining, in response to the maximum dose rate at the control point being greater than the maximum equipment dose rate, the maximum equipment dose rate as an equipment dose rate, and adjusting the rotation speed of the gantry based on the maximum equipment dose rate.

17. The device according to claim 16, wherein the method for determining the rotation speed of the gantry further comprises:
determining, in response to the maximum dose rate at the control point being less than or equal to the maximum equipment dose rate, the maximum dose rate at the control point as the equipment dose rate.

18. The device according to claim 16, wherein adjusting the rotation speed of the gantry based on the maximum equipment dose rate comprises:
determining movement time of the dosing system based on a difference value between dose values of two adjacent control points corresponding to the maximum dose rate at the control point and the maximum equipment dose rate; and
determining a target rotation speed based on the movement time of the dosing system and the gantry angles of the adjacent control points, and adjusting the rotation speed of the gantry to the target rotation speed.

19. A medical equipment, comprising: a processor, and a memory configured to store one or more programs or instructions executable on the processor, wherein the processor, when loading and executing the one or more programs or instructions, is caused to perform a method for determining a rotation speed of a gantry comprising:
acquiring control information of the gantry, wherein the control information of the gantry comprises leaf information and dose information of control points;
determining the rotation speed of the gantry and dose rates at the control points based on the leaf information and the dose information of the control points; and
adjusting the rotation speed of the gantry based on the dose rates at the control points and a maximum equipment dose rate.

20. A non-transitory readable storage medium, storing one or more programs or instructions, wherein the one or more programs or instructions, when loaded and executed by a processor, cause the processor to perform the method for determining the rotation speed of the gantry as defined in claim 1.

* * * * *